United States Patent [19]

Shiraiwa et al.

[11] 4,270,389
[45] Jun. 2, 1981

[54] METHOD AND APPARATUS FOR THE AUTOMATIC ULTRASONIC FLAW DETECTION

[75] Inventors: Toshio Shiraiwa; Hisao Yamaguchi; Shigeaki Matsumoto, all of Amagasaki; Masatoshi Tomabechi; Kimio Nakajima, both of Osaka, all of Japan

[73] Assignee: Sumitomo Metal Industries Limited, Osaka, Japan

[21] Appl. No.: 63,837

[22] Filed: Aug. 6, 1979

Related U.S. Application Data

[63] Continuation of Ser. No. 849,408, Nov. 7, 1977, abandoned, which is a continuation-in-part of Ser. No. 815,823, Jul. 14, 1977, abandoned.

[51] Int. Cl.³ .............................................. G01N 29/04
[52] U.S. Cl. ...................................... 73/612; 73/622; 73/1 DV
[58] Field of Search ................. 73/612, 620, 622, 637, 73/640, 1 DV

[56] References Cited

U.S. PATENT DOCUMENTS

| | | | |
|---|---|---|---|
| 2,969,671 | 1/1961 | Sproule | 73/612 |
| 3,041,872 | 7/1962 | Brown et al. | 73/612 |
| 3,575,042 | 4/1971 | Lovelace et al. | 73/620 |
| 4,106,326 | 8/1978 | Lather et al. | 73/1 DV |

OTHER PUBLICATIONS

V. V. Grebennikov et al., "The Sever Automatic System for the Ultrasonic Inspection of Welded Seams in Thickwalled Pipe," The Soviet Journal of Nondestructive Testing, vol. 10, No. 14, pp. 375-378, May 1975.

*Primary Examiner*—Anthony V. Ciarlante
*Attorney, Agent, or Firm*—Watson, Cole, Grindle & Watson

[57] ABSTRACT

Method and apparatus for automatic ultrasonic flaw detection of pipe welding zones wherein the width of the weld zone is divided into a plurality of subdivisions. The ultrasonic energy received from each of the subdivisions is displayed by employing multichannel gate circuitry providing respective outputs in units of 10% of the height of the echoes in each subdivision on a cathode ray tube in synchronization with signals representative of the longitudinal and lateral position of the probes along the pipe with respect to a reference point. The height of the defective echoes in each gate are printed together with the positions of the probe. The positions of the defects are diagrammed by a computer, thereby enabling high-speed data processing of the flaw detection information, a decrease in the time for the precise flaw detection comparable to conventional manual flaw detection method and apparatus and easy determination of the flaw detection results.

12 Claims, 9 Drawing Figures

```
  X     Y      GATE              X    Y      GATE 78.5   25.7   | | |2| | | | | |   19  22.4   | | |2| | | | | |
78.5   31.1   | | |232| | | |     18  25.5   | | |34| | | | |
78.5   34.5   | |29✕5| | | |      18  29.2   | | | |32| | | |
78.5   38.3   | | |9✕9| | | |     17  31.2   | |34| | | | | |
78.5   43.5   | | |597| | | |     17  27.6   | |56| | | | | |
78.5   46.4   | | |223| | | |     17  22.9   | | |2| | | | | |
78.5   57.9   | | |33| | | | |
78.5   62.1   | |23| | | | | |
```

METHOD AND APPARATUS FOR THE AUTOMATIC ULTRASONIC FLAW DETECTION

This is a continuation, of application Ser. No. 849,408 filed Nov. 7, 1977, now abandoned.

BACKGROUND OF THE INVENTION

1. Field of the Invention

The present invention relates to automatic and accurate method and apparatus capable of detecting flaws mainly in circumferential weld zones of pipe lines.

2. Description of the Prior Art

X-ray penetration testing has conventionally been applied for non-destructive inspection of weld zones. In conjunction with the improved performance of ultrasonic flaw detection apparatus, the application of ultrasonic flaw detection methods and techniques have recently been required for improved detection accuracy, shortened detection time, safe operation and decreased detection costs. In particular, in the non-destructive inspection of circumferential weld zones for high-pressure pipe lines, such weld zones have been inspected by the combined use of X-ray penetration testing and ultrasonic flaw detection techniques. Ultrasonic flaw detection has been performed mainly manually. However, manual ultrasonic flaw detection requres considerable skill and experience for the discrimination of the jamming echoes due to the weld bead, from the flaw echoes and also requires considerable technical skills. Under certain operational conditions, weld flaw detection has to be performed under severe conditions at sites such as common workshops where other operations are also being performed. Such conditions present intolerable burdens to the welding operations and inspectors.

In order to overcome such problems, it is desirable to automate welding flaw detection methods and techniques and also the associated necessary data processing, such as recording and evaluation and the like of the detected results.

SUMMARY OF THE INVENTION

It is an object of the invention in accordance with such requirements to provide automatic ultrasonic flaw detection methods and apparatus employing a calculator having an operational function to systematize the data processing of automatic ultrasonic flaw detection.

The method of the invention is characterized by dividing the width of a weld zone into a plurality of subdivisions. The ultrasonic energy reflected from each of the subdivisions is determined by employing multichannel gate circuitry having outputs in units of 10% of the height of the echoes in each subdivision which are displayed on a cathode ray tube in synchronization with signals representative of the positioning of the probe. The height of the defective echoes for each gate output are printed together with the position of the probe. The position of the welding defects are diagrammed by a computer, thereby enabling high-speed date processing and a decrease in the time required for precision flaw detection that is comparable to that of manual flaw detection, and easy determination of the flaw detection results. The method and apparatus of the invention is flexible and conveniently employed at any operation site.

The inventive method involves the circumferential movement of the flaw detector on a self propelled carrier, along a welding zone and performing the flaw detection by lateral movement of the probes with respect to the carrier. The position of the probes is displayed on an indicator, by means of multichannel gate circuitry having an output for each subdivision of the welding zone in units of 10% of the height of the echoes for each detecting range of the apparatus. The outputs from each of the mutichannel gates are displayed on a cathode ray tube in synchronization with the longitudinal and lateral positioning signals of the weld detection probes. The echoes digitized in the units of 10% of the height thereof. Those echoes having a height above a given threshold level are printed together with the circumferential and axial position of the probe to calculate the position of the flaw from the position of the probe and that gate output indicating the detection of a welding defect.

According to the flaw detection method of the invention, because the height of the defect echoes is printed together with the position of the detection probe, the diagramization of the flaw position is achieved by using a plotter, for example a mini-computer, and the determination and evaluation of the defects can be easily and precisely performed.

DETAILED DESCRIPTION OF THE PREFERRED EMBODIMENTS

The apparatus comprises the following components. A weld-following mechanism enables the flaw detection apparatus to track the weld zones with weld detection probe holders. Motors provide circumferential movement and scanning of the probe holders and the probes carried thereby. A detector enables determination of the position of the probes. A self-propelled carrier on which the probes are mounted detects flaws by axial scanning movements of the probes while the probes are moved along the circumferential weld zone at a predetermined speed (the maximum speed being about 3 m/min.). Display apparatus electrically displays the position of the probes and the height of the echoes. A data processing unit automatically prints the detection results.

The apparatus according to the invention is characterized, in particular, by the incorporation of a data processing unit comprising a calculator having reading and calculating functions for the high speed processing of the automatic ultrasonic flaw detector.

Figure 1:
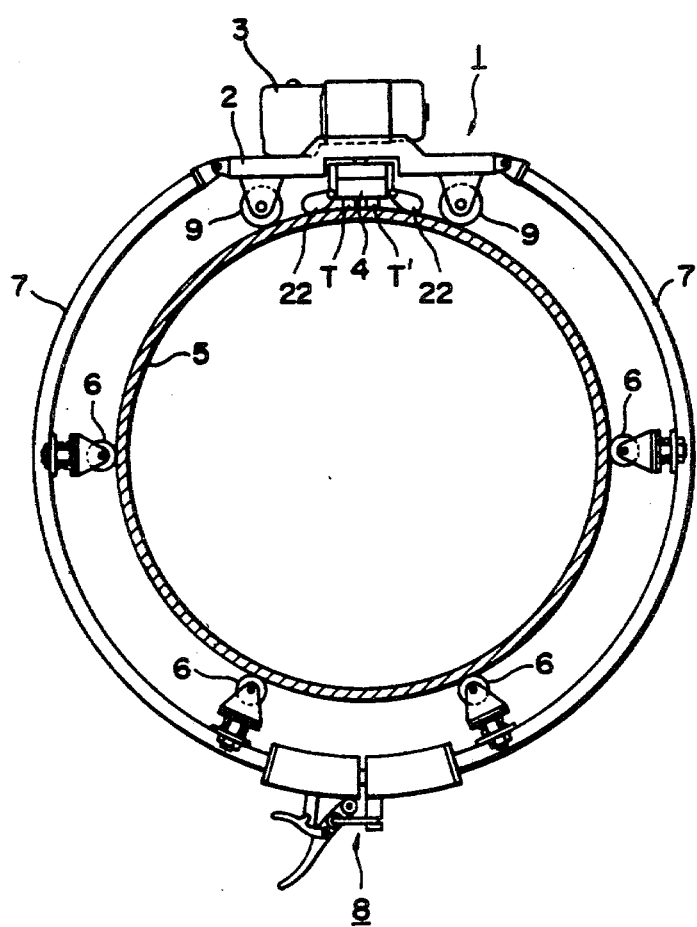
FIG. 1 is a side view of a self-propelled carrier flaw detection apparatus according to the invention.

As shown in FIG. 1, self-propelled carrier 1 is constructed so that probe holders 4 are mounted at the center portion of trestle 2, which is driven by motor 3 for circumferential movement of the trestle. Self-propelled carrier 1 is secured to the outer periphery of pipe 5, which is to be inspected, by a pair of semicircular holder bands 7, each of which is secured to trestle 2 at one end thereof, and includes a plurality of spaced rollers 6 for maintaining the trestle at a fixed distance from the outer periphery of pipe 6. Holder bands 7 are attached to one another by clamping units 8 attached at the opposing ends of each of the holder bands.

Figure 2:
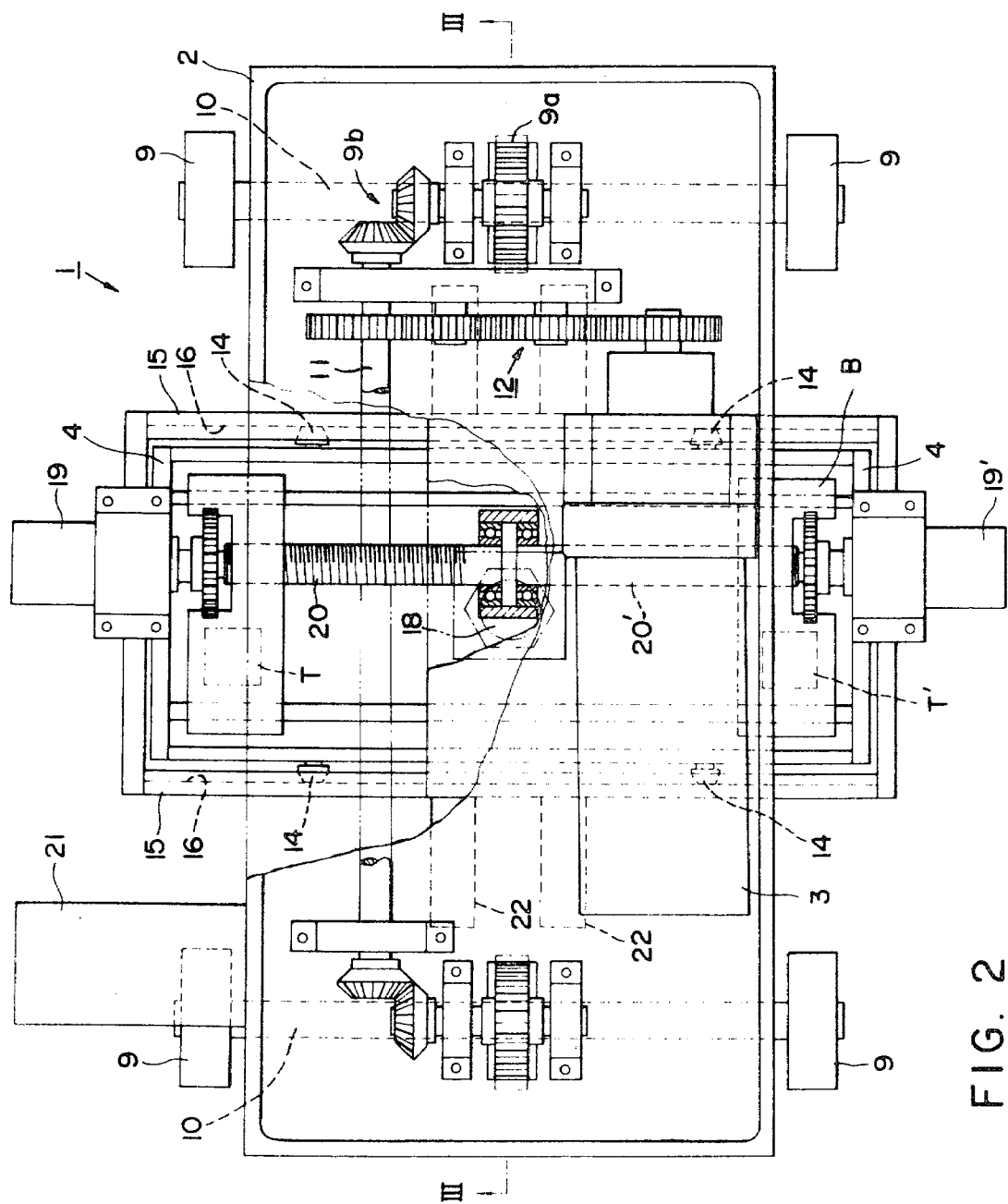
FIG. 2 is a partially cut-away plan view of the self-propelled carrier of FIG. 1 on an enlarged scale.
Figure 3:
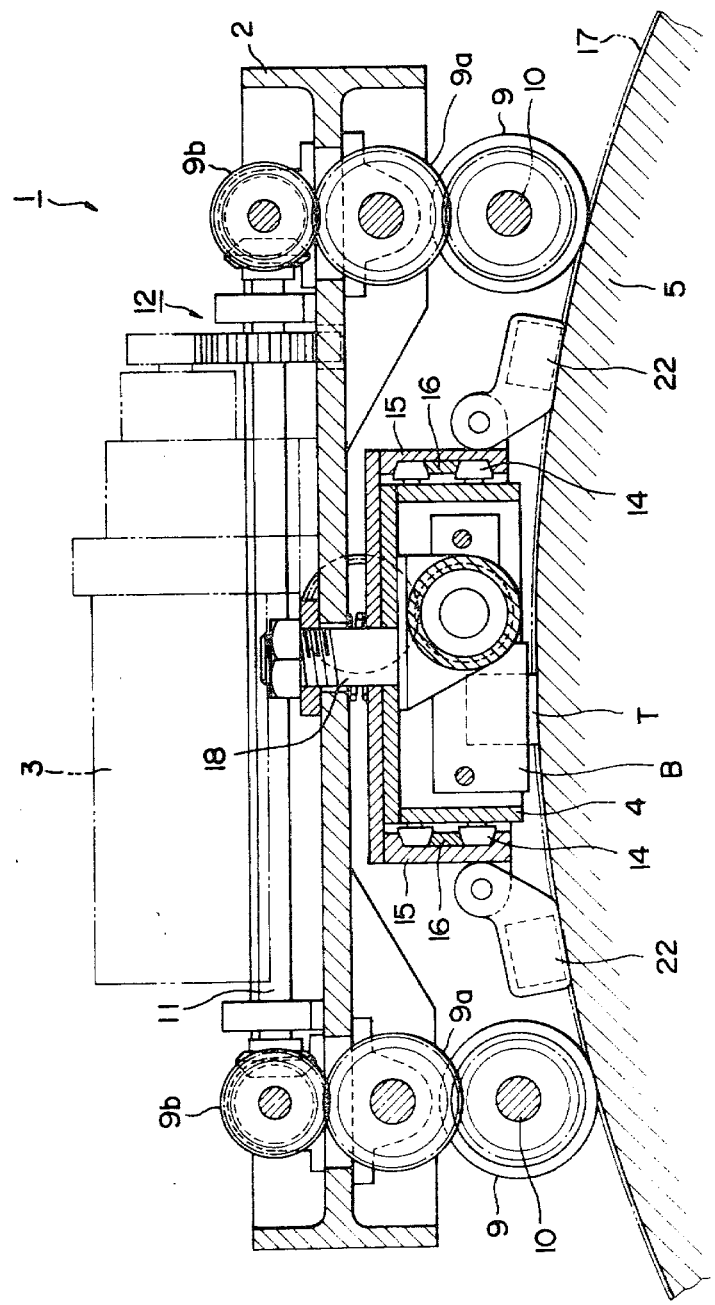
FIG. 3 is a longitudinal sectional view taken along line III—III in FIG. 2.

As shown in FIGS. 2 and 3, the travelling mechanism of the carrier comprises connecting four driven magnetic rollers 9, respectively mounted at both the front and rear ends of carrier 2, to respective driving shafts 10 driven by gears 9a, 9b which are, in turn, respectively connected to a transmission shaft 11 driven by reduction gears 12, connected to a shaft of motor 3. The mechanism is thus constructed so that one motor 3 can drive concurrently four magnetic rollers 9. It should be understood that such a mechanism is illustrated only as an exemplary embodiment and other suitable mechanisms can be employed, if desired.

Probe holder 4 travels on rails 16 attached to the inner walls of outer right and left frames 15 by multiple sets of roller mechanisms, each set including two rollers 14 mounted vertically with respect to one another. Probe holder 4 is suspended to be movable vertically and in a plane perpendicular thereto with respect to weld zone 17. Probe holder 4 is suspended by connecting outer frame 15 to supporting shaft 18, attached rotatably to carrier 2 through a recess defined at the central portion thereof as illustrated in FIGS. 2 and 3. Thereby, probe holder 4 is mounted on carrier 2 so as to be pivotable horizontally about supporting shaft 18 and to be horizontally movable, at the same time, in a direction perpendicular to weld zone 17.

A rotating shaft, constructed in two independently operable sections 20, 20' is threaded through a tapped hole in block B for mounting probes T, T' and each of the shaft sections 20, 20' is driven respectively by scanning motors 19, 19' secured to holder 4 so that either one, or both, probes T, T' can be independently or concurrently moved, as desired, by actuating either motor 19 or 19'. The displacement of both probes T, T' is measured by rotary encoder 21 which measures the axial scan position and the circumferential scan position of both probes T, T' in a manner known to those skilled in the art. Probes T, T' are movable because it is necessary to adjust the distance between end faces of the probes as the width of the weld bead is not constant due to the different radius of pipe to be inspected.

In the flaw detection of weld zones, it is essential to know the distance between the center of the weld bead and the point of incidence of the ultrasonic wave from the probes T and T'. It is necessary that a mechanism for following the weld bead be used in the automatic flaw detection apparatus. Such following mechanisms include optical and electrical types. As such mechanisms are too complex and large to be used in situ at the sites where the pipe lines are being inspected, the invention adopts a system wherein four magnets 22 are attached to outer frame 15 of probe holder 4 to be magnetically attracted to the pipe on both sides of weld zone 17, thereby enabling probes T and T' to follow the weld zone. Such a following or tracking mechanism is simple. Probes T, T' can be isolated from any vibration due to the close contact of magnets 22 with the outer surface of the pipe by means well known to those skilled in the art. Therefore, probes T, T' are always in contact with, or closely adjacent to, the surface of the pipe and the tracking of the probes with respect to the bead is kept within an accuracy of 2mm, which is sufficient such that no problem is encountered in the practical use of the system.

Probes T, T', according to the invention, each incorporate vibrator Ta for obliquely detecting flaws, and vibrator Tb for perpendicularly detecting the reflected waves from the bottom of the material. (see FIG. 5.) To avoid cluttering the drawing, only the electrical connectors to vibrator Tb are shown. The electrical connection to vibrator Ta are the same as those shown for vibrator Tb. Probes T, T' each function to maintain the flaw detecting sensitivity at a constant level by receiving the reflecting waves from the bottom of the material, i.e., the pipe to be inspected, namely from the radially confronting inner surface of the pipe, to calibrate the reflected waves in accordance with the change in the contacting conditions of the probe with the material due to the unevenness of the surface thereof. Specifically, the characteristics of the obliquely or perpendicularly incident ultrasonic energy into the material depends on the contacting conditions of the probe with the surface of the material to be inspected. The change in such contacting conditions causes fluctuation in the flaw detecting sensitivity, thereby leading to failures in the evaluation of welding defects. Therefore, it is necessary to calibrate the flaw detecting sensitivity to maintain it at a constant level. Taking such a requirement into account, the detector according to the invention employs vibrators Tb in each of probes T, T' which can calibrate the sensitivity automatically within a range of 20 dB. Such calibration is performed automatically by switching between vibrators Ta and Tb in each of probes T and T'.

Figures 4A, 4B, 4C, 6A, 6B:
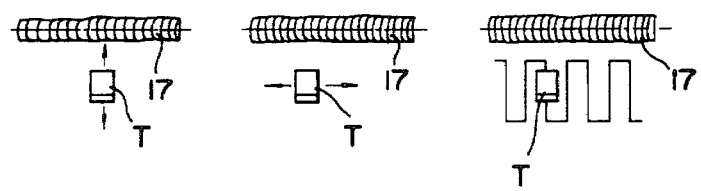
FIGS. 4A, 4B and 4C are illustrations showing respective scanning patterns of the probes of the self-propelled carrier in accordance with the invention.
FIGS. 6A, 6B show respective examples of the printed records of detected flaws as obtained from the printer in accordance with the invention.

FIGS. 4A, 4B and 4C show the scanning patterns for only one of probes T, T', as both probes scan in the same manner. FIG. 4A shows lateral or axial scanning, FIG. 4B shows longitudinal or circumferential scanning and FIG. 4C shows a scanning pattern representing the combined scanning patterns of FIGS. 4A and 4B (referred to hereinafter as rectangularly lateral scanning). Lateral or axial scanning performs sufficient flaw detection within a skip from 0.5 to 1.0 at a distance from the probe to the center of the bead ranging from 20 to 95 mm for pipes having a thickness t ranging from 8 to 15 mm. The pitch for rectangularly lateral scanning can also be adjusted to a minimum of 1 mm.

Figure 5:
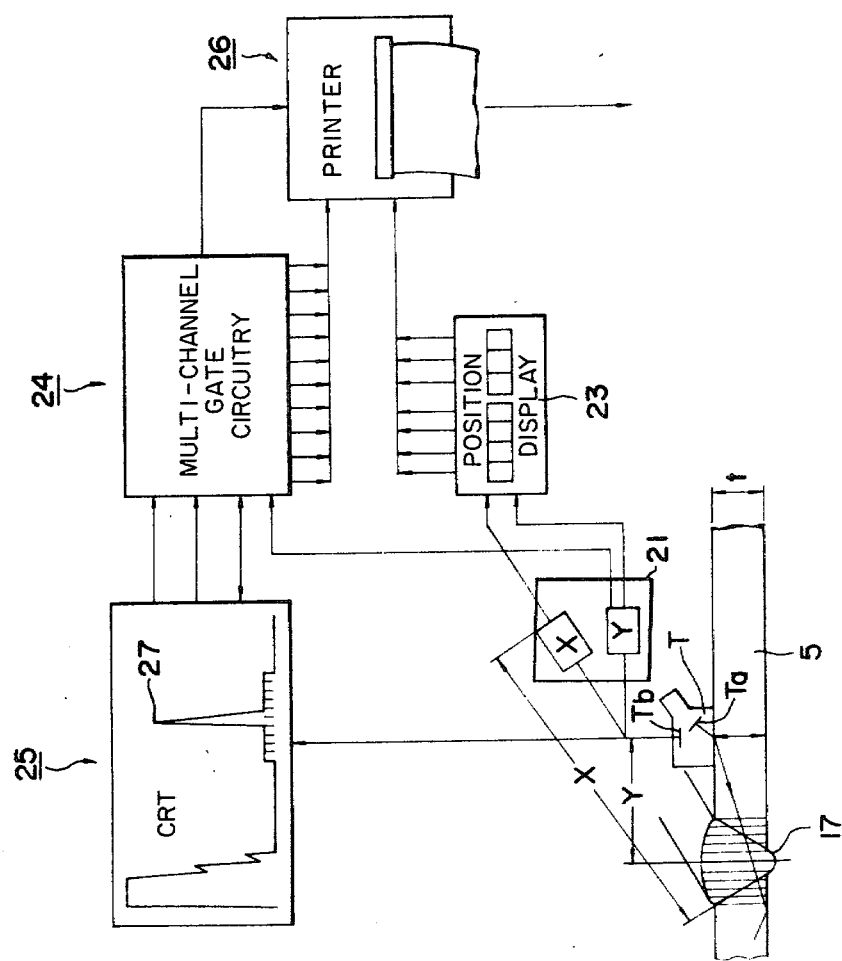
FIG. 5 is a block diagram showing the data processing apparatus according to the invention.

As shown in FIG. 5, the data processing unit for obtaining the results from the automatic ultrasonic flaw detector comprises position display 23 which indicates the X and Y coordinates of the position of probes T, T', namely scanning laterally in the axial direction (Y) and longitudinally, circumferentially (X) around the pipe with respect to weld zone 17. Multichannel gate circuitry 24, may for example as illustrated include the channel gates providing outputs in 10% units of the echo amplitude from each subdivision of the weld zone, defined by subdividing the width of the weld zone into a plurality of subdivisions. Cathode ray tube 25 displays the echo amplitudes from the ten channel gates in multichannel gate circuitry 24 in synchronization with the signals indicating the respective position of the probes. Printer 26 prints the echo amplitudes of any welding defects that are present, as determined by the ten channel gate output, together with the position of the probes.

In the operation of the automatic flaw detecting apparatus using the aforedescribed detector, self-propelled carrier 1 is mounted on pipe 5 over weld zone 17, which is to be inspected. After setting the correct distance from the welded bead to the probes T, T', carrier 1 is conveyed circumferentially in the direction X alongside the welded bead. Probes T, T' are laterally moved in the axial direction Y relative to weld zone 17 to carry out the flaw detection. The positions of the probes are displayed by position display 23 and at the same time, the echo amplitudes are displayed on cathode ray tube 25. The display of the probe signals from either probe T or T' can be selectively displayed by a switch (not shown) in accordance with teachings well known to those skilled in the art. The presence of echo 27 indicates a defect within any of the channel gates of multi-channel gate circuitry 24. The displayed echoes are always in synchronization with the lateral and longitudinal movement of the probes. The amplitudes of such echoes are digitized in 10% units and printer 26 prints out the echo amplitudes having levels higher than a predetermined threshold value.

Exemplary printed records of welding defects detected by the present detector are shown in FIGS. 6A and 6B, wherein FIG. 6A shows lateral scanning relative to the axial direction and FIG. 6B shows an example of rectangularly lateral scanning at a scanning distance of 1 mm. FIG. 6A shows the results of the flaw detection when the probe was positioned at a point 78.5 mm from a reference point on the circumference of the pipe, which was scanned laterally relative to the axial direction over ten subdivisions of the weld zone width. If an echo representing a defect is present within the ten channel gates, the echo amplitude will be digitized in 10% units so that numeral 1 represents 10%, numeral 2 represents 20% of the echo height, and so forth. The asterisks represent echo amplitudes greater than 100%. In FIG. 6A, the higher values recorded within the portion enclosed by a solid line, namely from the third gate to the sixth gate, indicates that a number of defects are found within the third to the sixth zones of the ten subdivisions in the weld zone. Similarly, the rectangularly lateral scanning pattern, FIG. 6B, indicates that a number of defects are present within the portion enclosed by the solid line, namely, from the second to the fifth zones, at distances 17 to 18 mm from a reference point.

In summary, according to the invention, a weld zone is scanned by probes movable laterally with respect to the axial direction of the longitudinal movement along the weld zone of a self-propelled carrier on which the probes are mounted. The echo amplitudes of welding defects present within each gate output, associated with a subdivision of the weld zone, is synchronized with the position coordinates of the probes on a printer so that approximate conditions of the welding defects are indicated during the flaw detection operation and the distribution of the welding defects can be observed at a glance to concurrently determine the severity of the defects to be classified. In addition, the self-propelled carrier on which the detector is mounted has a structure enabling detection of welding defects in a constantly stable manner, so that the accuracy of the flaw detection apparatus and method is very high. Furthermore, it is possible to graphically depict the depth of welding defects, echo amplitudes, the length and severity of the welding defects incorporating a mini-computer in accordance with the foregoing description.

We claim:

1. A method for automatically detecting flaws in circumferentially extending pipe welding zones, comprising the steps of:
   moving a welding flaw detector in at least two different directions in tracking relationship to a weld zone;
   subdividing the width of said weld zone into a plurality of areas;
   transmitting pulsed energy obliquely to said weld zone from a first transmitter, and alternately periodically transmitting pulsed energy perpendicularly to said weld zone from a second transmitter;
   periodically calibrating the flaw detection using the energy transmitted from said second pulse transmitter;
   generating output signals from a plurality of gate circuits each respectively responsive to the echo signals produced by said pulsed energy from a specified one of said areas;
   generating position signals representative of the position of said flaw detector from a reference point; and
   displaying said output signals and said position signals in associated relationship to indicate any welding flaws and their respective positions in each one of said plurality of areas of the weld zone.

2. A method as in claim 1, further comprising the step of recording said output signals and said position signals in associated relationship to indicate any welding flaws and their respective positions in the weld zone.

3. A method as in claim 2 wherein said step of generating output signals includes the step of limiting the amplitude of those output signals representing echoes exceeding a given threshold value to a percentage of their normal amplitude and further comprising the steps of digitizing said reduced amplitude signals and said position signals prior to said step of displaying.

4. A method as in claim 3, wherein the flaw detector is movably mounted on a self-propelled carrier and said step of moving includes the steps of propelling said carrier circumferentially in tracking relationship to said weld zone and moving said flaw detector transversely with respect to the movement of said carrier.

5. A method as in claim 4, wherein said step of digitizing said position signals includes the step of generating digital signals representative of the position of said flaw detector in both the circumferential and transverse directions of movement thereof.

6. A method as in claim 5, wherein said steps of displaying and recording include the respective display and recording of said digital position signals in relation to the associated amplitude levels for each of said subdivided areas.

7. Apparatus for automatically detecting flaws in circumferentially extending pipe welding zones, comprising:
   a welding flaw detector movable in at least two different directions in tracking relationship to a welding zone;
   means for transmitting pulsed energy to said weld zone, including a first pulse transmitter for transmitting pulsed energy obliquely to said weld zone and a second pulse transmitter for alternately periodically transmitting pulsed energy perpendicularly to said weld zone;
   means for periodically calibrating the apparatus by using the echoes received from the pulsed energy from said second transmitter;
   means for generating output signals from a plurality of gate circuits each respectively responsive to the echoes produced by said pulsed energy from a respective one of a like plurality of areas subdividing the width of said welding zone;

means for generating position signals representative of the position of said flaw detector from a reference point; and means for displaying said output signals and said position signals in associated relationship to indicate any welding flaws and the respective position thereof in each one of said plurality of areas in the weld zone.

8. Apparatus as in claim 7 further comprising means for recording said output signals and said position signals in associated relationship to indicate any welding flaw and the respective position thereof in the weld zone.

9. Apparatus as in claim 8 wherein said means for generating output signals includes means for limiting the amplitude of those output signals representing echoes exceeding a threshold value to a percentage of their normal amplitude; and further comprising means for digitizing the reduced amplitude signals and said position signals.

10. Apparatus as in claim 9 further comprising a self-propelled carrier for mounting said flaw detector and including means for propelling said carrier circumferentially in tracking relationship to said weld zone and moving said flaw detector transversely with respect to the movement of said carrier.

11. Apparatus as in claim 10 wherein said means for digitizing said position signals includes means for generating digital signals representative of the position of said flaw detector in both the circumferential and transverse directions thereof.

12. Apparatus as in claim 11 wherein said means for displaying and said means for recording respectively include means for displaying and means for recording said digital position signals in relation to the associated amplitude levels of each of said subdivided areas.

* * * * *